(12) United States Patent
Krasnobaev et al.

(10) Patent No.: US 6,888,128 B2
(45) Date of Patent: May 3, 2005

(54) VIRTUAL WALL GAS SAMPLING FOR AN ION MOBILITY SPECTROMETER

(75) Inventors: Leonid Ya. Krasnobaev, Newton, MA (US); Stephen N. Bunker, Wakefield, MA (US)

(73) Assignee: Implant Sciences Corporation, Wakefield, MA (US)

( * ) Notice: Subject to any disclaimer, the term of this patent is extended or adjusted under 35 U.S.C. 154(b) by 0 days.

(21) Appl. No.: 10/754,088

(22) Filed: Jan. 7, 2004

(65) Prior Publication Data

US 2004/0155181 A1 Aug. 12, 2004

Related U.S. Application Data (63) Continuation-in-part of application No. 10/295,010, filed on Nov. 14, 2002.
(60) Provisional application No. 60/363,485, filed on Mar. 12, 2002, provisional application No. 60/357,618, filed on Feb. 15, 2002, and provisional application No. 60/357,394, filed on Feb. 15, 2002.

(51) Int. Cl.$^7$ .......................... H01J 49/40; H01J 49/28; B01D 59/44
(52) U.S. Cl. ...................... 250/281; 250/288; 250/287; 250/290; 250/294
(58) Field of Search ................................ 250/281, 288, 250/287, 290, 294, 286

(56) References Cited

U.S. PATENT DOCUMENTS

| | | | | |
|---|---|---|---|---|
| 4,060,001 A | * | 11/1977 | Archerd ..................... | 73/863.11 |
| 4,311,669 A | * | 1/1982 | Spangler ...................... | 422/98 |
| 4,551,624 A | * | 11/1985 | Spangler et al. ............ | 250/287 |
| 4,797,554 A | * | 1/1989 | Blanchard et al. .......... | 250/287 |
| 5,218,203 A | * | 6/1993 | Eisele et al. ................. | 250/288 |
| 5,420,424 A | * | 5/1995 | Carnahan et al. ........... | 250/287 |
| 5,736,739 A | * | 4/1998 | Uber et al. .................. | 250/287 |
| 5,763,876 A | * | 6/1998 | Pertinarides et al. ........ | 250/288 |
| 6,068,749 A | * | 5/2000 | Karger et al. ............... | 204/452 |
| 6,177,669 B1 | * | 1/2001 | Wells et al. ................. | 250/288 |
| 6,512,224 B1 | * | 1/2003 | Miller et al. ................ | 250/286 |

OTHER PUBLICATIONS

U.S. Appl. No. 10/853,563, filed May 25, 2004, Pulsed Vapor Desorber, Belyakov et al.
U.S. Appl. No. 10/295,039, filed Nov. 14, 2002, Radiative Sample Warming for an Ion Mobility Spectrometer, Motchkine et al.
U.S. Appl. No. 10/349,491, filed Jan. 22, 2003, Explosive Detection System, Krasnobaev et al.
U.S. Appl. No. 10/818,434, filed Apr. 5, 2004, Modified Vortex for an Ion Mobility Spectrometer, Krasnobaev et al.
U.S. Appl. No. 10/890,820, filed Jul. 14, 2004, Flash Vapor Sampling for a Trace Chemical Detector, Belyakov et al.

\* cited by examiner

*Primary Examiner*—John R. Lee
*Assistant Examiner*—Kalimah Fernandez
(74) *Attorney, Agent, or Firm*—Choate, Hall & Stewart LLP (57) ABSTRACT

The presence of trace molecules in air may be determined using an ion mobility spectrometer. Such devices may be used in the fields of explosives detection, identification of narcotics, and in applications characterized by the presence of very low airborne concentrations of organic molecules of special interest. The sensitivity of such instruments may depend upon on the method of gas sampling utilized. A virtual wall gas sampling system can greatly improve the sampling efficiency, particularly when the sampling needs to be performed at a distance from the air intake and large volumes need to be sampled. The virtual wall gas sampling system consists of an intake gas flow and a separate group of one or more sheet-like gas flows, which may be either mutually deflected to move with a circular motion or may be formed into a cylindrical bounding surface.

27 Claims, 5 Drawing Sheets

VIRTUAL WALL GAS SAMPLING FOR AN ION MOBILITY SPECTROMETER

CROSS-REFERENCE TO RELATED APPLICATIONS

This application is a continuation-in-part of U.S. application Ser. No. 10/295,010, filed Nov. 14, 2002, which is incorporated herein by reference and which claims benefit and priority from U.S. Provisional Application No. 60/357,394, filed Feb. 15, 2002, U.S. Provisional Application No. 60/357,618, filed Feb. 15, 2002, and U.S. Provisional Application No. 60/363,485, filed Mar. 12, 2002, all of which are incorporated herein by reference.

BACKGROUND OF THE INVENTION

1. Field of the Invention

This invention relates to a gas sampling system and more particularly to a gas sampling system for an ion mobility spectrometry (IMS) instrument that detects chemicals present as vapors in air or other gases, or liberated as vapors from condensed phases such as particles or solutions, when the source of vapors is at a distance from the entrance orifice of the IMS.

2. Description of Related Art

IMS instruments operate on the basis of the time taken by ionized molecules to move through a gas-filled drift region to a current collector while under the influence of an electric field. The ions are created in a gas-filled region called the ion source, which is connected to the drift region through an orifice or a barrier grid. The ion source may use any of a variety of techniques to ionize atoms and molecules. One or more flowing streams of gas enter the ion source through one or more orifices, and the gas may exit through one or more different orifices. At least one of the flowing gas streams entering the ion source includes gas that has been sampled (the "sample gas") from the surrounding atmosphere or other source of vapor to be analyzed.

In some cases, the process of taking a sample begins with an operator rubbing an absorbent substance, such as chemical filter paper, onto the surface to be tested. Particles of the chemical of interest may then be transferred and concentrated on the absorber. This intermediate absorber may then be brought to the vicinity of the sampling orifice of the IMS. However, this method of concentrating using an absorbent substance is deficient in that it tends to be relatively slow to implement and is subject to variations in the skill of the operator. Additionally, while the absorber is relatively low in cost, the process of taking a great many samples becomes expensive in that the absorber generally should only be used once to ensure consistent results.

The instrument's sampling method uses a gas pump, which draws the sample gas into the ion source through a tube. For example, the pump may be disposed to provide a partial vacuum at the exit of the ion source. This partial vacuum may be transmitted through the confines of the ion source and appear at the entrance orifice of the ion source. A further tubulation may be provided as an extension to a more conveniently disposed sampling orifice external to the IMS. The operator may place a sample in the near vicinity of this external sampling orifice, and the ambient vapor may be drawn into the gas flow moving towards the ion source.

Sometimes molecules of interest undesirably adsorb onto surfaces in the sampling flow path. Therefore, it is sometimes useful to minimize unnecessary surfaces between the sampling orifice and the ion source. This is why, in some cases, the gas pump is often disposed in the gas flow stream following the ion source, rather than preceding the ion source.

The existing methods of gas sample collection are deficient in that it is difficult to adequately sample from a large volume unless the volume is a semi-sealed solid enclosure. Excessive dilution of the gas sample often occurs when the atmosphere is allowed to freely enter the space being sampled. Avoiding solid walls can be important in applications where wall surface contamination can be significant or the presence of nearby walls is unpleasant to the contained object or undesirable. The present invention particularly addresses the problem of large volumes, providing virtual walls to seal the sampled volume from the atmosphere.

SUMMARY OF THE INVENTION

According to the present invention, an embodiment of a gas sampling system for an ion mobility spectrometer includes a first gas pump that provides a gas flow at a partial gas vacuum compared to ambient gas pressure, a second gas pump that provides a gas flow at a partial gas pressure compared to the ambient gas pressure, a first orifice that provides the partial gas vacuum external to said ion mobility spectrometer, tubulation means connecting the first orifice to said ion mobility spectrometer, a plurality of orifices for the partial gas pressure which are concentric and external to the first orifice, means for producing sheet-like gas flows from the plurality of orifices such that the outward projected axis of the first orifice is enclosed within the sheet-like gas flows, and means for directing the sheet-like gas flows with the normal axes of the sheet-like gas flows being substantially perpendicular to the axis defined by the first orifice and enclosing in part a gas sampling volume. The partial gas vacuum may be within 50 millimeters of mercury (50 Torr) of the ambient gas pressure. The sheet-like flow may be provided by an air knife, air curtain, or an air door. The means for directing the sheet-like flow may be provided by a nozzle, by the Coanda effect or by deflection vanes. The sheet-like flow may be substantially cylindrical in shape or in the shape of at least one planar surface. The sheet-like flow may optionally be directed slightly outward from the axis of said first orifice to compensate for the inward force due to the pressure differential across said sheet-like flow.

According further to the present invention, a gas sampling system for an ion mobility spectrometer includes a first gas pump providing a gas flow at a partial gas vacuum compared to ambient gas pressure, a second gas pump providing a gas flow at a partial gas pressure compared to the ambient gas pressure, a first orifice for said partial gas vacuum which is external to said ion mobility spectrometer, tubulation means connecting said first orifice to said ion mobility spectrometer, a plurality of orifices for said partial gas pressure which are concentric and external to said first orifice, means for producing sheet-like gas flows from said plurality of orifices such that the outward projected axis of said first orifice is enclosed within the sheet-like gas flows, and means for directing said sheet-like gas flows with the normal axes of the sheet-like gas flows being substantially perpendicular to the axis defined by said first orifice and enclosing in part a gas sampling volume. The sheet-like flow may be provided by an air knife, a nozzle, an air curtain, or an air door. The means for directing the sheet-like flow may be provided by the Coanda effect or by deflection vanes. The plurality of sheet-like flows may induce a vortex about the projected axis of said first orifice.

According further to the present invention, a gas sampling system includes an ion mobility spectrometer having a sampling orifice and at least one sheet-like gas flow source that creates at least one sheet-like gas flow virtual wall beyond the sampling orifice, the at least one sheet-like gas flow virtual wall forming at least part of the boundary of an enclosed volume used for gas sampling. The ion mobility spectrometer may operate at substantially ambient gas pressure. A gas pump may draw a gas flow through the sampling orifice and generates a vacuum within 50 millimeters of mercury (50 Torr) of the substantially ambient gas pressure. A plurality of sheet-like air flow sources may provide a plurality of sheet-like air flows that form a rotary air flow in either the clockwise or counterclockwise direction. The gas sampling system may also include a gas pump connected to the orifice that causes gas from inside the enclosed volume to flow into the ion mobility spectrometer.

Having the plurality sheet-like air flow sources may provide a plurality of sheet-like air flows that form a rotary flow in either the clockwise or counterclockwise direction may be preferable to the case in which some members of the plurality of sheet-like air flows may flow in the counter-rotating direction. The gas sampling system including a gas pump connected to the orifice that causes gas from inside the enclosed volume to flow into the ion mobility spectrometer provides a tangentially-projected cyclone, tornado, or vortex.

According further to the present invention, a gas sampling system includes at least one source that produces at least one sheet-like air flow used to define an enclosed sample volume and an orifice coupled to said enclosed sample volume, the orifice providing a partial vacuum to cause gas to flow from within the enclosed sample volume to said orifice. The sheet-like flow may be provided by an air knife, an air curtain, an air door, a nozzle, the Coanda effect, or deflection vanes.

According further to the present invention, a method of sampling gas includes forming an enclosed volume around the gas using at least one virtual wall provided by a sheet-like air flow and receiving gas for sampling from within the enclosed volume. A plurality of sheet-like air flows may be provided. The sheet-like air flows may flow in a direction having an axis of rotation that is substantially parallel to a direction of gas flow in connection with receiving gas from within the enclosed volume. The at least one sheet-like air flow may be in a direction that is substantially parallel to a direction of gas flow in connection with receiving gas from within the enclosed volume or may be in a direction that is substantially parallel, but slightly radially outward, to a direction of gas flow in connection with receiving gas from within the enclosed volume. The method may include, after receiving gas for sampling, providing the gas to an ion mobility spectrometer.

Another embodiment of the invention applies to an ion mobility spectrometer that uses an external sampling orifice to draw in vapors to be analyzed. In addition to this existing orifice, a coaxial orifice may be provided which emits gas towards the object to be sampled. Said emitted gas is further deflected such that it is induced to move in a circular flow about the axis of the external sampling orifice. A further component of the motion is a net velocity away from the external sampling orifice. This type of flow may be often referred to as a cyclone. The spinning motion may result in a radially-outward directed centrifugal force that restrains the emitted gas flow from immediately being drawn radially inward into the partial vacuum of the external sampling orifice. Eventually, friction with the surrounding ambient gas may slow the emitted gas sufficiently that it will be drawn into the partial vacuum at some distance from the external sampling orifice. Depending on the flow of the emitted gas, this distance can be varied from near the external sampling orifice (low flow) to far from the external sampling orifice (high flow). The cyclonic motion in effect creates a tube consisting of a virtual wall of moving gas that behaves like an extension of the tube that formed the external sampling orifice. An embodiment in which the cyclone air flow is projected from the axial end of the resultant cyclone may be referred to as an axially-projected cyclone, tornado, or vortex.

BRIEF DESCRIPTION OF THE DRAWING

The invention is described with reference to the several figures of the drawing, in which.

DETAILED DESCRIPTION

When operating conventional IMS systems, increasing the sample gas flow rate increases the volume of gas sampled in a given amount of time, which can result in more sensitive detection. However, a higher sample gas flow rate also increases the velocity of the gas through the ion source, and too high a velocity can interfere with the performance of the IMS. In addition, a sampling orifice having the general form consisting of the end of a hollow tube will draw gas from locations disposed both directly in front of the orifice as well as locations disposed to the side of the orifice. The partial vacuum supplied by the gas pump declines rapidly to ambient gas pressure within a short distance from the sampling orifice, because gas is flowing into the orifice from many directions.

In some circumstances, it is desirable for IMS instruments to be able to sample vapors at a distance from the external sampling orifice. Examples may include, but are not limited to, sampling of vapor from complex surfaces that contain many holes, crevices, or deep depressions, people and animals that prefer not to be rubbed by absorbent material, large three dimensional objects, textured materials such as cloth, surfaces that must be sampled in a short time, and surfaces in which surface rubbing by human operators is inconvenient or expensive.

In addition, the sampling orifice may become contaminated with vapor-emitting particles if the sample inadvertently contacts the orifice. Such contamination is particularly difficult to remove in a short period of time, thus preventing continuous operation of the instrument. Such contamination could be avoided if vapors could be sampled at a distance from the sampling orifice, but sampling from a distance tends to substantially dilute the sampled gas and thus to reduce sensitivity.

The distance where vapors may be sampled beyond the sampling orifice may be increased by increasing the sample gas flow rate, i.e., increasing the pumping speed. However, besides the interference with the performance of the ion source of the IMS caused by high velocity flow, this method dilutes the concentration of the desired sample vapor by mixing in a much larger volume of ambient gas. Therefore, the sensitivity of the IMS may decline if the sample gas flow rate is increased excessively.

The sampling of vapors with the ordinary sampling orifice is not highly directional. This is normally of little consequence in conventional detectors, since the volume being sampled must normally be disposed very near to the orifice, and directionality is provided by moving the orifice to another location.

Figure 1:
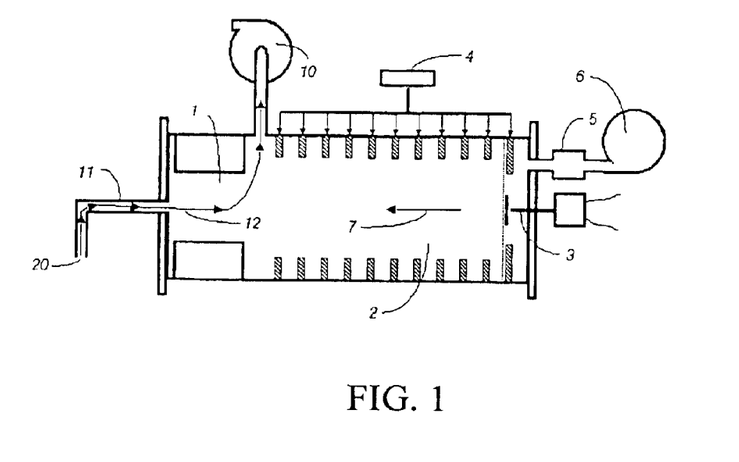
FIG. 1 is a schematic of the conventional IMS detector.

A conventional IMS, which may be used in connection with the system described herein, is illustrated in FIG. 1. The IMS consists of an ion source 1, a drift tube 2, a current collector 3, a source of operating voltage 4 and a source of purified drift gas 5, possibly with its own gas pump 6. Conventionally, an IMS will already include a gas pump for gas sampling 10 and a tubular connection 11 between the ion source 1 and an external gas sampling orifice 20. Gas flow for the drift gas 7 moves through the drift tube 2. Sampling gas flow 12 moves from the external gas sampling orifice 20 through the tubular connection 11 and ion source 1 to the gas sampling pump 10. The IMS may operate at substantially ambient gas pressure (i.e., at ambient atmospheric pressure and at pressures relatively close to ambient atmospheric pressure).

Figure 2:
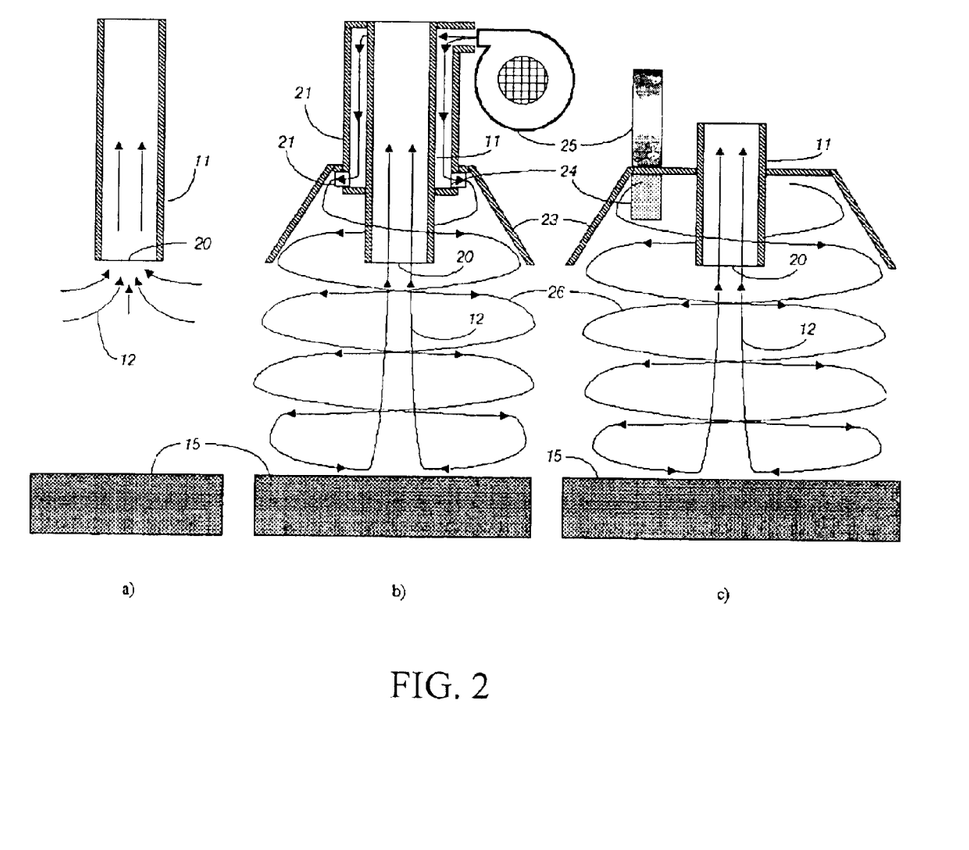
FIG. 2a is a schematic showing gas flow in a conventional gas sampling system not using a cyclonic flow.
FIG. 2b is a schematic showing a cyclone gas sampling system with a cone-shaped nozzle using deflection vanes.
FIG. 2c is a schematic showing a cyclone gas sampling system with a cone-shaped nozzle using tangential gas flow.

A conventional gas sampling system is shown in FIG. 2a. The gas pump for vacuum 10 may be disposed elsewhere and is not shown in the figure. The portion of the tubular connection 11 nearest the external gas sampling orifice 20 is shown. The sampling gas flow 12 shows that the volume of gas being sampled is disposed near to the external gas sampling orifice 20, and gas is being drawn into the orifice 20 over an angular range between substantially perpendicular to the axis of the orifice to on the axis of the orifice 20. When the target surface 15 is disposed at a distance greater than 1–2 times the diameter of the external gas sampling orifice 20, the quantity of sampled gas is either very small or highly diluted by the more abundant gas sampled from nearer the external gas sampling orifice 20.

A cyclone gas sampling system in which the cyclone is projected from an end of the cyclone axis includes the following components as shown in FIGS. 2b and 2c. A partial vacuum relative to ambient gas pressure is supplied by a gas pump (not shown). The gas pump may be disposed at some distance from the cyclone gas sampling system with the vacuum being guided to the cyclone gas sampling system by means of a tubulation or conduit 11. The gas pump and corresponding tubulation 11 may already be part of an existing IMS. A partial pressure relative to ambient gas pressure is supplied by a gas pump 25. The gas pump 25 may be disposed at some distance from the cyclone gas sampling system with the pressure being guided to the cyclone gas sampling system by means of a tubulation or conduit 21. It is preferable that the pressure gas pump is separate from the vacuum gas pump to avoid cross-contamination of the sample gas between the two gas flows. The pressure gas flow 26 is induced to move in a circular, cyclonic motion away from the cyclone gas sampling system by a fluid rotator. The fluid rotator may include, for example, gas deflection vanes (shown in FIG. 2b), or a hollow, cylindrically or conically shaped orifice 23 concentric with the orifice for the partial vacuum 20. An alternate embodiment is to introduce the pressure gas flow through an orifice 24, which is oriented tangential to the hollow cylindrically or conically shaped orifice 23 and is deflected into a circular flow by means of the curvature of the inside wall. The pressure gas flow orifice 24 may be singular or a plurality of such orifices. The gas pump 25 may also be singular or a plurality of such pumps. Other means for inducing rotary flow of a gas, such as a turbine, are known in the art and are also included within the scope of the invention.

The axis of the emitted cyclonic gas flow defines the axis for guiding the partial vacuum from the external sampling orifice. If the axis of the emitted cyclonic flow is tilted over a small angular range, the partial vacuum due to the flow at the external sampling orifice follows this tilting motion, effectively scanning the position of the virtual gas sampling location. This characteristic is useful for sampling over a one dimensional stripe or a two dimensional surface area without moving the IMS from a fixed location.

Figure 3:
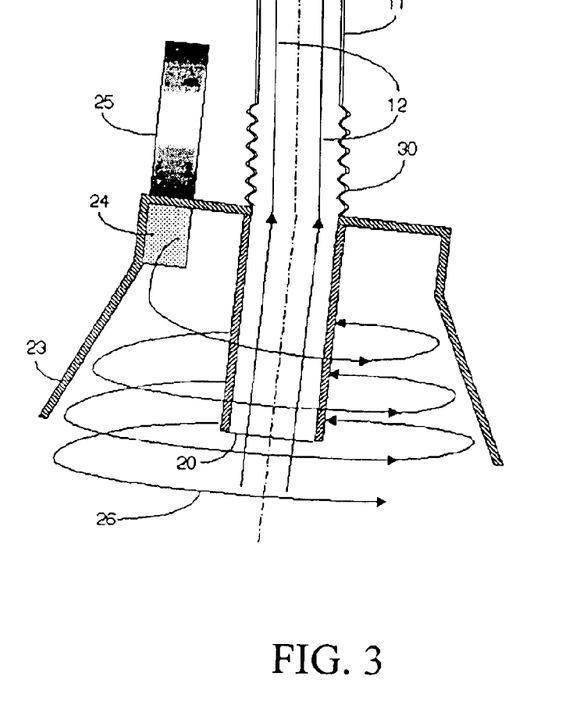
FIG. 3 shows a plurality of cyclones arranged in a rectilinear grid.

FIG. 3 shows one possible embodiment of a tilted cyclone in which the gas sampling tubulation 11 is flexible. Other possible embodiments would include, but not be limited to a ball joint within tubulation 11, a tilting cylindrical or conical surface 23 with the tubulation 11 fixed, and dynamic control of the relative velocities of a plurality of gas flows 26. As an alternative embodiment, one of the two axes of a two dimensional surface area could be scanned by mechanical movement of the object being scanned, perhaps along a track or moving belt. The second scan axis, perpendicular to the mechanically scanned axis, would be provided by tilting the cyclone orifice. This method is useful for minimizing the number of IMS instruments required to fully sample a given surface.

Cyclonic flow when combined with a vacuum may collect particles. The emitted gas flow generally exhibits a quasi-chaotic motion, which may dislodge larger particles from a surface. Once dislodged, the particles may become entrained in the gas flow towards the external sampling orifice. Depending on the application, such particles may or may not be desirable. For example, particles entering the ion source of the IMS may adhere to surfaces and continue to emit vapor for a long period of time, thus causing a continuous erroneous response. A limited range of particle sizes, about 0.5 to 10 micrometers in diameter, may be removed within the tubulation connecting the external sampling orifice to the ion source using electrostatic precipitation. Larger particles tend to be rejected radially outward due to the centrifugal force of the cyclone gas flow. Smaller particles cannot easily be rejected from the sampled gas.

The problem of contamination from particles may also be lessened by heating the tubulation connecting the external gas sample orifice to the ion source. The ion source may also be heated. Heating causes more rapid vaporization or sublimation of the contamination particles, thus shortening the time period of vapor emission and more rapidly cleansing the gas sampling system. As an alternate embodiment, the tubulation 11 may be designed to be an expendable component that is easily removed for cleaning or replacement.

An advantage of the axially-projected cyclone gas sampling method for IMS is that the system is light in weight, which is important for handheld sampling devices. Compared to existing sampling methods, one or more extra gas pumps are needed, but the power requirements are only a few Watts or less for most applications. An extra pump may also serve other functions in the IMS system, such as drawing cooling air from over a heated surface.

The axially-projected cyclone sampling system may be utilized singly or by means of a plurality of axially-projected cyclone sampling systems. The external gas orifice may be a single tubulation connected to a single ion source and IMS or there may be tubular branches leading from a single ion source to greater than one cyclone sampling system. Alternately, multiple ion sources plus IMS's plus cyclone sampling systems may be disposed proximally in order to more efficiently sample a larger surface area in a shorter period of time.

Figure 4:
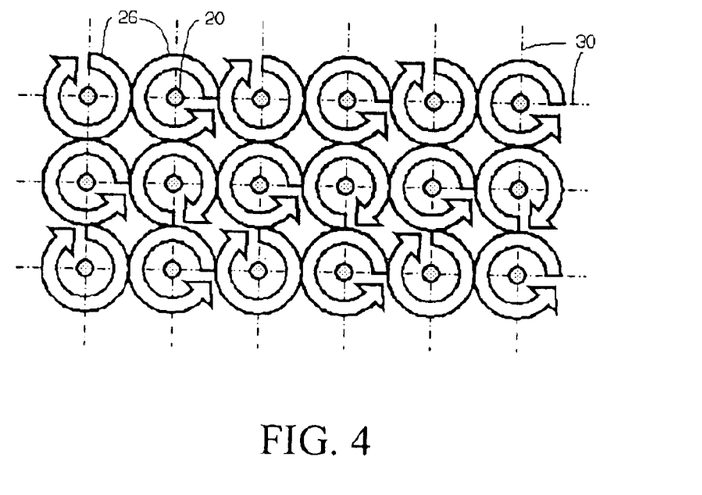
FIG. 4 shows an embodiment of a cyclone nozzle that may be scanned on at least one axis.

FIG. 4 shows one possible layout of a plurality of axially-projected IMS instruments. In this case a two dimensional grid is used in which the crossing points of the centering lines 40 is the location of an IMS instrument. The external gas sampling orifice 20 is indicated for each instrument. The circular direction of cyclone gas flow 26 is also indicated as preferably alternating clockwise and counterclockwise for neighboring instruments in order for the neighboring gas flows 26 to always be in the same direction.

When axially-projected cyclone sampling systems are disposed proximally, neighboring cyclones preferably have rotational directions of the cyclonic gas flow that are oppositely oriented in order not to have the gas flows cancel each other at the boundary.

The gas flow of the gas emitted into the axially-projected cyclone may be deflected into a circular flow by several possible means. Fractions of the total emitted gas flow may be selectively deflected by means of individually oriented vanes, such that the net resulting gas flow is circular. Alternatively, a hollow cone or cylinder may be employed with a gas flow entering the cone or cylinder at a tangential angle. The inside walls of the hollow cone or cylinder then act as the deflector, constraining the gas flow along a circular path while within the confines of the hollow cone or cylinder. When the emitted gas expands beyond the hollow cone or cylinder, the partial vacuum of the external sampling gas orifice provides the force required to constrain the emitted gas flow from moving tangentially away from the central axis.

Figure 5:
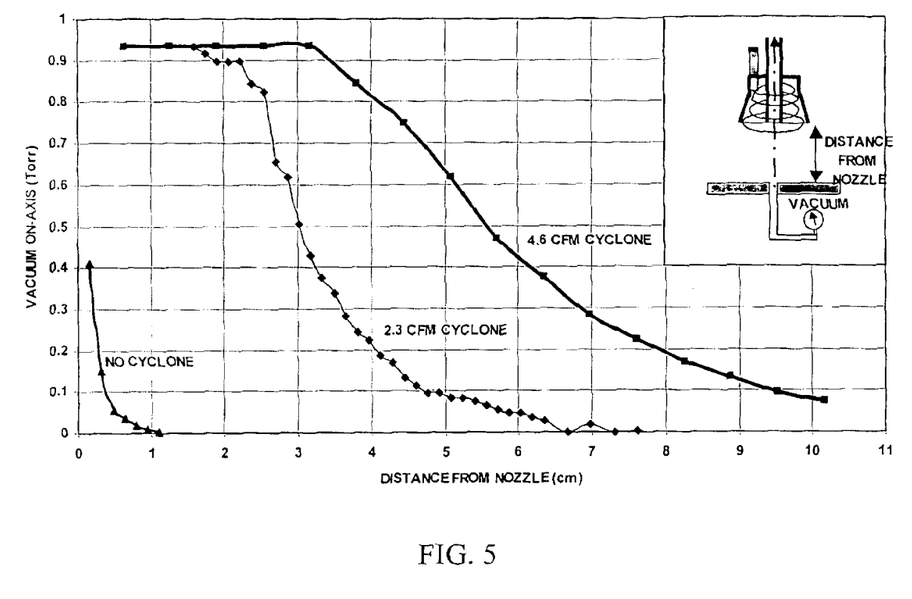
FIG. 5 shows partial vacuum measured on an axis of an external gas sampling orifice for no cyclone, for a 0.6 Watt cyclone with 2.3 cfm air flow, and for a 1.2 Watt cyclone with 4.6 cfm air flow.

FIG. 5 shows the measured vacuum below ambient gas pressure for three different flow rates of the cyclone gas for an axially-projected flow. The external sampling gas orifice is 1.6 centimeters in diameter, and the greatest possible value for vacuum for the gas pump used in this measurement is about 1 Torr (1 millimeter of mercury) less than the ambient gas pressure. When no cyclone flow is present, 10% of maximum vacuum (0.1 Torr) occurs at a distance equal to about 0.25 times the external sampling gas orifice diameter. With a cyclone gas flow equal to 2.3 cubic feet per minute (cfm), the corresponding distance for 10% of maximum vacuum equals about 3.0 times the external sampling gas orifice diameter. With a cyclone gas flow equal to 4.6 cfm, the corresponding distance for 10% of maximum vacuum equals about 5.9 times the external sampling gas orifice diameter. This demonstrates that the length of the virtual extension of the gas sampling tubulation is proportional to the gas flow of the cyclone.

Figure 6:
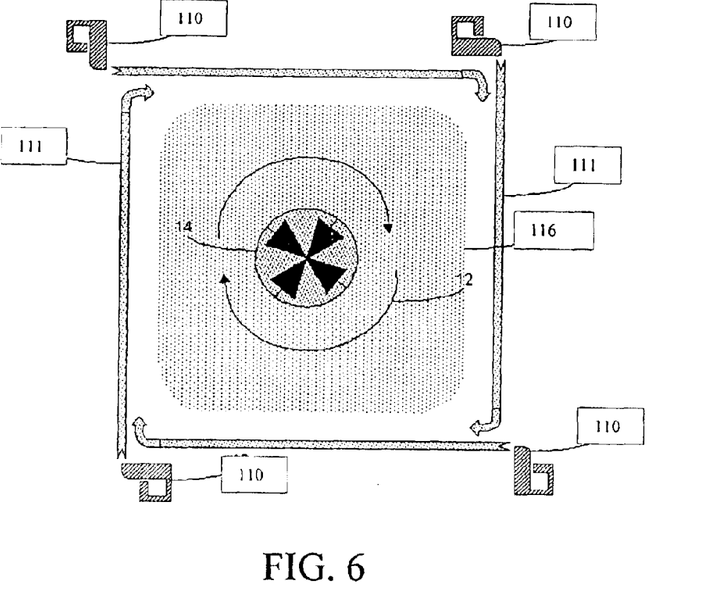
FIG. 6 is a schematic showing an axial view of a large volume virtual wall gas sampling system with tangential sheet-like airflow.

FIG. 6 illustrates an alternative embodiment of a gas sampler that may be used with the ion mobility spectrometer of FIG. 1 or may be used with other systems that sample gas.

FIG. 6 shows an axial view of a virtual wall sheet-like airflow 111 disposed tangential to the enclosed sample volume 116. The normal axis of flow of the sheet-like airflow 111 is disposed substantially perpendicular to the axis of the external sampling orifice 20 (not shown in this view) of the ion mobility spectrometer. FIG. 6 shows an example of four such sheet-like airflows 111, which together form the circumferential walls of a box-like volume. Each sheet-like airflow 111 is provided by a sheet-like air flow source 110, such as an air knife. The source 110 is illustrated as consisting of a manifold emptied through a narrow slit aperture followed by a curved surface employing provide the Coanda effect. Of course, other mechanisms may be used as sources, such as different types of nozzles, air knives, air curtain generators, air doors, other devices that provide the Coanda effect, deflection vanes, and other appropriate devices. In addition, any number of sources may be used to provide the system described herein. For example, two air knives disposed on opposing sides combined with two solid surfaces disposed on the perpendicular axis to form four sides of a box would provide entrance and exit air doors for a gas sampling volume.

A sheet-like flow may be defined as originating from one or more sources whose combined aperture is substantially greater on one axis compared to the perpendicular axis and whose half-maximum flow divergence angle on the substantially smaller axis is less than 25 degrees at a distance of 30 centimeters from the source. A sheet-like flow may be straight or curved on the longer axis. An air knife may be provided by a manifold for pressurized air with an exit nozzle in which one axis is substantially smaller than the perpendicular axis. For example, an air knife may have a nozzle aperture that is tens of centimeters by 0.05 centimeters. An air knife may be straight or curved on the larger axis. An air knife may be combined with various means to deflect the air flow, such as a nozzle, a surface employing the Coanda effect, or deflection vanes. An air door or air curtain may be provided by a plurality of closely spaced nozzles disposed along a line, such that the combined aperture of the array may be a few centimeters by many tens of centimeters. The Coanda effect is the tendency of a thin sheet-like air flow to follow the contour of a one-sided bounding surface until a discontinuity is encountered.

The sheet-like air flow may form at least one bounding surface for a gas sampling volume. In embodiments disclosed herein, the sheet-like air flow does not intentionally impact or wipe any target objects within the gas sampling volume. The sheet-like air flow may provide a barrier separating the external atmosphere from the internal gas sampling volume, which is at a lower pressure than the external atmosphere. A heater (not shown) that heats the sheet-like air flow may be optionally included. Other means for adding ions may also be used. The heater or other means for adding ions may be provided by an appropriate device or technique familiar to one of ordinary skill in the art. Heating the sheet-like air flow may cause increased target vapor emission. Ions may be used to assist in the release of particles from target surfaces.

The directions of flow are illustrated in FIG. 6 as inducing a clockwise circulation, which creates a vortex. The vacuum pump 14 of the ion mobility spectrometer causes a flow of the sampled gas 12 to enter into the external sampling orifice 20 (not shown in this view). The enclosed sample volume 116 is bounded by the sheet-like airflows 111, as seen in this view.

Figure 7:
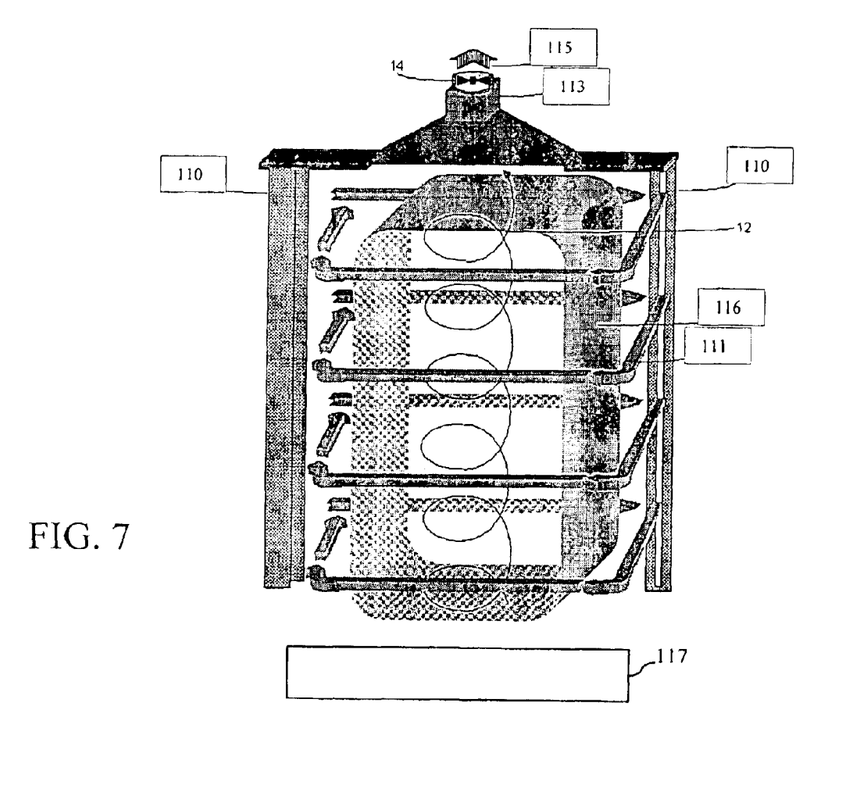
FIG. 7 is a schematic showing a side view of a large volume virtual wall gas sampling system with tangential sheet-like airflow.

FIG. 7 shows a side view of the virtual wall gas sampler shown in FIG. 6. The sources 110 of the sheet-like airflows 111 have a length that defines the third axis of the enclosed sample volume 116. The length of the sources 110 can be arbitrarily long, so the gas sampling volume can be varied over a wide range of sizes. In some embodiments, one or more of the sources 110 may have a different length than others of the sources 110. A surface of a target 117 defines another face of the enclosed sample volume 116. It is also possible in other instances for multiple surfaces of the target 117 to define multiple faces of the enclosed sample volume 116. A solid surface associated with and proximal to the external sampling orifice 20 (not shown in this view) defines the last surface around the enclosed sample volume 116. Together, these surfaces create an enclosure that substantially prevents external atmosphere from entering and diluting the gas within the enclosed sample volume 116. The sheet-like airflows 111 are virtual walls, and therefore are not contaminated with vapors or particles of the target species. An exhaust 115 of the vacuum pump 14 causes a flow of the sampled gas through a gas sampling device 113, such as the IMS devices discussed elsewhere herein.

It is recognized that virtual walls created from the sheet-like airflows 111 and solid surface walls may be interchangeable in whole or in part, and the example shown in FIGS. 6 and 7 does not limit the choice for which walls are solid or virtual. For example, FIG. 7 shows a solid surface pyramidal duct connectable to the external sampling orifice 20 to provide one end of the enclosed sample volume 116. This surface, for example, could also be reproduced with virtual walls to avoid contamination and the need to warm solid surfaces to desorb target vapors.

Figure 8:
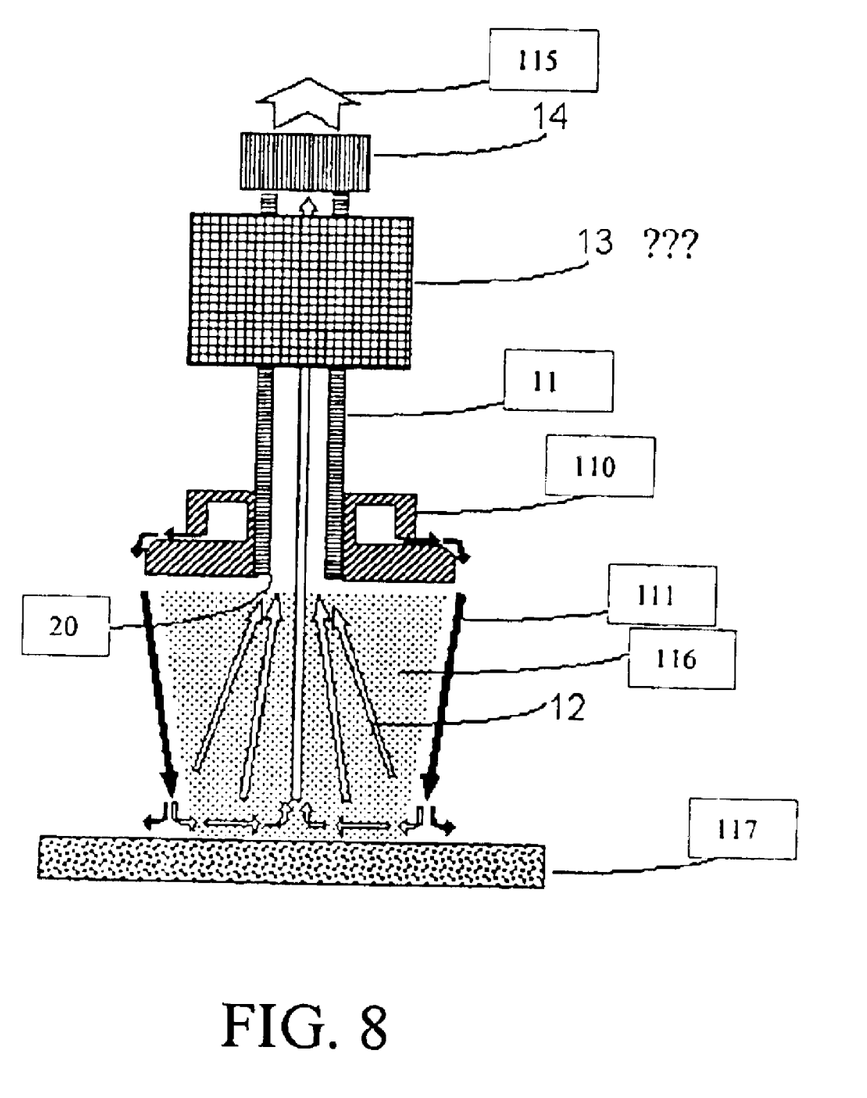
FIG. 8 shows the virtual wall gas sampling system using projected air walls.

FIG. 8 shows an alternate embodiment in which the sheet-like airflows 111 are projected substantially parallel to the axis of flow into the external sampling orifice 20. As before, an enclosed volume 116 is defined by the sheet-like airflow 111, the solid surface in the near vicinity of the external sampling orifice 20, and the surface of the target 117. The direction of projection of the sheet-like airflow 111 may also be disposed slightly outward radially from the axis of flow into the external sampling orifice 20 to partially correct for the constriction of the sheet-like airflow 111 due to the pressure differential between the external pressure of the atmosphere and the partial vacuum within the enclosed sample volume 116. FIG. 8 shows an embodiment in which a single ring-shaped air knife is the source 110 of the sheet-like airflow 111. Other embodiments may employ multiple sources 110. Since the sheet-like airflow 111 is being projected away from the external sampling orifice 118, at some distance the enclosed volume will contract to a point, because the flow velocity decreases with distance, and there is a constant inward force due to the pressure differential across the sheet-like airflow 111. In an alternate embodiment of this form of the virtual wall, the sheet like airflow 111 may also be deflected at the source 110 with a rotational velocity component to produce a sheet-like cyclone, tornado, or vortex. This type of geometry may be suitable for portable or handheld sampling, where the enclosed volume 116 does not need to be very large. The size of the enclosed volume 116 will be approximately proportional to the air pressure applied to the sources 110 of the sheet-like airflow 111.

Note that the techniques and systems described herein may be combined so that, for example, the cyclonic sampling system illustrated in FIG. 2(b), FIG. 2(c), FIG. 3, or FIG. 4 may be used in connection with the virtual wall gas sampling system of FIG. 6., FIG.7 or FIG. 8. Other appropriate combinations of the systems and techniques described herein are also possible and within the abilities of one of ordinary skill in the art.

The IMS instrument described herein may incorporate other novel features, such as the improved laser ion source described in copending and commonly assigned U.S. Provisional Application 60/357,618, filed Feb. 15, 2002, or the electrostatic particle sampling system described in copending and commonly assigned U.S. Provisional Application 60/363,485, filed Mar. 12, 2002. These related provisional applications are incorporated by reference herein.

Other embodiments of the invention will be apparent to those skilled in the art from a consideration of the specification or practice of the invention disclosed herein. It is intended that the specification and examples be considered as exemplary only, with the true scope and spirit of the invention being indicated by the following claims.

What is claimed is:

1. A gas sampling system for an ion mobility spectrometer comprising:
   a first gas pump that provides a first gas flow at a partial gas vacuum compared to ambient gas pressure;
   a second gas pump that provides a second gas flow, different from said first gas flow, at a partial gas pressure compared to the ambient gas pressure;
   a first orifice in communication with the first gas pump to provide the first gas flow in a first gas flow direction toward the first gas pump, wherein the first gas flow is external to said ion mobility spectrometer;
   tubulation means connecting said first orifice to said ion mobility spectrometer;
   a plurality of orifices in communication with said second gas pump to provide said second gas flow that substantially surrounds said first gas flow to increase vacuum at a sampling location distal from the first orifice and;
   means for directing said second gas flow in a direction with a normal axis of said second gas flow and a direction of flow both being substantially perpendicular to said first gas flow direction and enclosing in part a gas sampling volume.

2. A gas sampling system as in claim 1 wherein said partial gas vacuum is within 50 millimeters of mercury (50 Torr) of the ambient gas pressure.

3. A gas sampling system as in claim 1 wherein said second gas flow is provided by an air knife.

4. A gas sampling system as in claim 1 wherein said second gas flow is provided by an air curtain.

5. A gas sampling system as in claim 1 wherein said second gas flow is provided by an air door.

6. A gas sampling system as in claim 1 wherein said means for directing said second gas flow is provided by a nozzle.

7. A gas sampling system as in claim 1 wherein said means for directing said second gas flow is provided by the Coanda effect.

8. A gas sampling system as in claim 1 wherein said means for directing said second gas flow is provided by deflection vanes.

9. A gas sampling system as in claim 1 wherein said second gas flow may be at least one of: substantially cylindrical in shape or in the shape of at least one planar surface.

10. A gas sampling system as in claim 1 wherein said second gas flow is directed slightly outward from the axis of said first orifice to compensate for the inward force due to the pressure differential across said second gas flow.

11. A gas sampling system as in claim 1 wherein said second gas flow induces a vortex about said first gas flow.

12. A gas sampling system, comprising:
an ion mobility spectrometer having a sampling orifice through which a sampling gas flow passes in a sampling gas flow direction; and
at least one sheet-like gas flow source that creates at least one sheet-like gas flow virtual wall that is different from the sampling gas flow and is beyond the sampling orifice, the at least one sheet-like gas flow virtual wall forming at least part of a boundary of an enclosed volume used for gas sampling, wherein a normal axis of the sheet-like gas flow is substantially perpendicular to the sampling gas flow direction and wherein a flow direction of the sheet-like gas flow is also substantially perpendicular to the sampling gas flow direction.

13. A gas sampling system, according to claim 12, wherein the ion mobility spectrometer operates at substantially ambient gas pressure.

14. A gas sampling system according to claim 12, wherein a gas pump draws the sampling gas flow through the sampling orifice and generates a vacuum within 50 millimeters of mercury (50 Torr) of the substantially ambient gas pressure.

15. A gas sampling system according to claim 12, wherein a plurality of sheet-like air flow sources provide a plurality of sheet-like air flows that form a rotary air flow in either the clockwise or counterclockwise direction.

16. A gas sampling system according to claim 12, further comprising:
a gas pump connected to the orifice that causes the sampling gas flow from inside the enclosed volume to flow into the ion mobility spectrometer.

17. A gas sampling system, comprising:
at least one source that produces at least one sheet-like air flow used to define an enclosed sample volume; and
an orifice coupled to said enclosed sample volume, said orifice providing a partial vacuum to cause gas to flow in a sampled gas direction from within said enclosed sample volume to said orifice, wherein the sampled gas direction is substantially perpendicular to both a direction of flow of the sheet-like air flow and a normal axis to the sheet-like air flow.

18. A gas sampling system as in claim 17 wherein said sheet-like flow is provided by an air knife.

19. A gas sampling system as in claim 17 wherein said sheet-like flow is provided by an air curtain.

20. A gas sampling system as in claim 17 wherein said sheet-like flow is provided by an air door.

21. A gas sampling system as in claim 17 wherein said sheet-like flow is provided by a nozzle.

22. A gas sampling system as in claim 17 wherein said sheet-like flow is provided by the Coanda effect.

23. A gas sampling system as in claim 17 wherein said sheet-like flow is provided by deflection vanes.

24. A method of sampling gas, comprising:
forming an enclosed volume around the gas using at least one virtual wall provided by a sheet-like air flow; and
receiving a sampling gas flow moving in a sampling gas flow direction for sampling from within the enclosed volume, wherein a normal axis to the sheet-like air flow is substantially perpendicular to the sampling gas flow direction and wherein a direction of flow of the sheet-like air flow is also substantially perpendicular to the sampling gas flow direction.

25. A method, according to claim 24, further comprising:
providing a plurality of sheet-like air flows.

26. A method, according to claim 25, wherein the sheet-like air flows flow in a rotary direction having an axis of rotation that is substantially parallel to a direction of gas flow in connection with receiving gas from within the enclosed volume.

27. A method, according to claim 24, further comprising:
after receiving gas for sampling, providing the gas to an ion mobility spectrometer.

* * * * *